United States Patent [19]

Broadwin et al.

[11] Patent Number: 4,978,333
[45] Date of Patent: Dec. 18, 1990

[54] RESONATOR FOR SURGICAL HANDPIECE

[75] Inventors: Alan Broadwin, Brooklyn, N.Y.; Claus Kleesattel, San Jose, Costa Rica

[73] Assignee: Valleylab, Inc., Boulder, Colo.

[21] Appl. No.: 287,749

[22] Filed: Dec. 20, 1988

[51] Int. Cl.⁵ ............................................. A61M 1/00
[52] U.S. Cl. ................................... 604/22; 128/24 A; 51/59 SS; 310/26
[58] Field of Search ...................... 128/24 A; 604/22; 366/127; 310/26; 51/59 SS

[56] References Cited

U.S. PATENT DOCUMENTS

| Re. 25,033 | 8/1961 | Balamuth et al. | |
| 2,826,396 | 3/1958 | Murdoch, Jr. | 366/127 |
| 3,311,352 | 3/1967 | Dostal | 310/26 |
| 3,370,186 | 2/1968 | Antonevich | 366/127 |
| 3,375,583 | 4/1968 | Blank et al. | 128/24 A |
| 4,223,676 | 9/1980 | Wuchinich et al. | |
| 4,330,278 | 5/1982 | Martin | 128/24 A |
| 4,425,115 | 1/1984 | Wuchinich | 604/22 |

FOREIGN PATENT DOCUMENTS 855917 7/1949 Fed. Rep. of Germany ........ 310/26

Primary Examiner—William E. Kamm
Assistant Examiner—K. M. Pfaffle
Attorney, Agent, or Firm—Peter C. Richardson; Lawrence C. Akers; Mark Dryer

[57] ABSTRACT

An ultrasonic resonant vibrator comprising an ultrasonic vibration magnetostrictive transducer, and a resonant member having a proximal end and a distal end for transmitting ultrasonic vibrations to an operating member which is part of the resonant structure. The vibrator comprises an integral substantially rigid column having a central axis with fins extending radially relative to said axis and having a longitudinal hole defining a tunnel centered along the central axis, wherein at least part of the resonant member is located within the tunnel; and a surgical handpiece incorporating such a vibrator.

6 Claims, 1 Drawing Sheet

RESONATOR FOR SURGICAL HANDPIECE

BACKGROUND OF THE INVENTION

This invention relates to an ultrasonic resonant vibrator, particularly to an ultrasonic resonant vibrator including an improved magnetostrictive transducer for use in a surgical handpiece.

Apparatus incorporating an ultrasonic resonant vibrator is known in the art for surgical use, particularly for surgical handpieces comprising tools for fragmenting tissue. In such apparatus the required ultrasonic vibrations may be produced by magnetostrictive means transmitted through a connecting member to an appropriate tool.

A representative example of such an apparatus is disclosed in U.S. Pat. No. 4,223,676, the disclosure of which is incorporated herein by reference. In the apparatus disclosed in U.S. Pat. No. 4,223,676 the magnetostrictive transducer is a magnetostrictive stack composed of a sandwich of nickel alloy strips such as is taught in U.S. Pat. No. RE 25,033. The said stack comprises a plurality of elongated strips of magnetostrictive material, i.e. nickel alloy, forming a laminated structure. The laminations are necessary to reduce adverse effects, e.g. energy loss from eddy currents.

In a later improved design the laminated stack was made with a shallow curved profile for added rigidity.

In order to function properly, a laminated transducer preferably:
1. should be mechanically stiff:
2. have minimum acoustic losses; and
3. should be relatively easy to handle away from its operating environment.

The prior art transducer described above has proved to be effective and highly serviceable in its use in surgical procedures. However, despite its good performance record it still has certain disadvantages. For example, the flat laminated structure tends to overheat if the flow of coolant is reduced for any reason and such overheating may result in serious damage to the apparatus. Also the flat construction gives substantial mechanical stiffness in only one plane. This lack of overall rigidity may result in mechanical damage due to mishandling and, if the laminations become separated or bent, the entire apparatus may be rendered useless.

The above disadvantages may be overcome if the transducer is made in the form of a substantially rigid column comprising elongated strips arranged in the form of radially extending fins as described and claimed in application Ser. No. 287,748, filed concurrently herewith and the disclosure of which is incorporated herein by reference.

The improved magnetostrictive transducer of Ser. No. 287,748 comprises a plurality of elongated strips of magnetostrictive material, each strip having a proximal end, a distal end and a substantially V-shaped cross section wherein each arm of the V is formed by the longitudinal length of the strip, each strip being attached to an adjacent strip at both the proximal end and the distal end to form an integral substantially rigid column having a central axis with fins extending radially relative to said axis.

It has now been found that a still further improved ultrasonic resonant vibrator incorporating a finned magnetostrictive, transducer as disclosed in Ser. No. 287,748 is provided if said transducer is made to have a central tunnel of sufficiently large diameter to accommodate at least part of a resonant member, especially the connecting portion which transmits the ultrasonic vibrations to the operating member, e.g. a surgical tool or a conduit for fluid movement It further has been found that it is immaterial for the efficient operation of the final device whether said connecting portion is attached externally, end-to-end, to the transducer, or attached internally, as hereinafter described, in a configuration which is herein termed a "folded resonator".

SUMMARY OF THE INVENTION

In accordance with the present invention there is provided an ultrasonic resonant vibrator comprising a resonant member having a proximal end and a distal end and an ultrasonic vibration magnetostrictive transducer for generating ultrasonic vibrations which are transmitted from said transducer to said resonant member, wherein said transducer comprises a plurality of elongated strips of magnetostrictive material, each strip having a proximal end, a distal end and a substantially V-shaped cross section, wherein each arm of the V is formed by the longitudinal length of the strip, each strip being attached to an adjacent strip at both the proximal end and the distal end to form an integral substantially rigid column having a central axis with fins extending radially relative to said axis and having a longitudinal hole defining a central tunnel centered along said central axis, wherein at least part of said resonant member is located within said tunnel and is attached at its said proximal end to an inside end of said tunnel.

Preferably, said resonant member comprises a connecting portion having a proximal end and a distal end, wherein said proximal end corresponds to the proximal end of the resonant member and said distal end is adapted to be connected to an operating member.

The cross section of the central tunnel may be of any suitable configuration which is symmetrical about the central axis and is adapted to accommodate a resonant member having a compatible cross section. Examples of suitable cross sections are circular and square. For convenience and practicality, a substantially circular cross section is preferred.

Preferably, each of the elongated strips of the transducer is of substantially V-shaped cross section and each arm of the V is formed by the longitudinal length of the strip. In a preferred embodiment, the attachment of each strip at its ends is made by brazing or welding. It is also preferred that each arm of each V-shaped strip is in touching contact with an arm of an immediately adjacent strip along the complete longitudinal length of the strip to form a radially extending fin and the resulting fins form a radial pattern around said central tunnel extending the length of the resulting substantially rigid column.

A particularly preferred embodiment is a vibrator in which the resonant member comprises the combination of a connecting portion or member connected to an operating member and said operating member is a surgical tool. In this embodiment the members form a part of a surgical handpiece which, by utilizing the folded resonator, is appreciably shorter than conventional handpieces and consequently, less cumbersome and easier to handle than prior art handpieces.

In another embodiment, the combination of the operating member and the connecting portion may be substituted by a resonant tool to provide a surgical handpiece.

Preferably, the vibrator has a central hole extending along its length and said hole has a diameter large enough to accommodate a tube for transporting fluid.

DETAILED DESCRIPTION OF THE INVENTION

In contrast to the conventional laminated stack of the prior art, the transducer used in the vibrator of the present invention is in the form of a substantially rigid column, preferably of substantially circular cross section, having a longitudinal central tunnel centered along a central axis, and fins extending radially relative to said axis Said fins are formed by elongated strips of magnetostrictive material, for example a nickel alloy having a suitable oxide coating, attached to each other at their distal and proximal ends, preferably by brazing or welding.

In a preferred embodiment, each of the elongated strips is of substantially V-shaped cross section and the said column is formed by aligning each strip so that one of the arms thereof is in touching contact with an arm of the immediately adjacent strip along its complete longitudinal length so that the touching strips form a radial pattern of fins around said central tunnel extending the length of the column. The resulting structure is a substantially rigid column which is stiffer than the laminated stack of the prior art and moreover the fin arrangement provides a plurality of free surfaces which facilitate heat loss and thereby reduce the possibility of overheating if the normal cooling means should fail.

Although the V-shaped cross section is particularly preferred for the longitudinal strips, strips of any other suitable cross section may be used. The V shape is particularly suitable because of ease of fabrication of the individual strips, simplicity of construction of the columnar configuration and higher rigidity compared to other shapes using a plurality of such strips.

The column formed when the strips are attached to each other at their ends has a central tunnel extending along its length, and at least part of a resonant member is located within said tunnel and is attached at its proximal end to an inside end of said tunnel. In a particularly preferred embodiment of the invention the part of the resonant member located within the central tunnel comprises a connecting portion and hereinafter the invention will be more particularly described with reference to this preferred embodiment. The attachment of the connecting portion to an end of said tunnel may be made by screwing, brazing or welding and, if desired may be performed at the same time as the brazing or welding of the ends of the elongated strips which form the transducer.

Additionally, the vibrator may include a central hole extending along its length, which hole has a diameter large enough to accommodate a tube for transporting aspiration or irrigation fluid. Thus, said tube will enter the vibrator through the proximal end of the transducer and extend along the central axis of the connecting portion and into the operating member, e.g. surgical tool, attached to the distal end of said connection portion.

The preferred vibrator according to the invention is particularly adapted to be used in a surgical handpiece comprising a surgical tool connected through a connecting portion to an ultrasonic vibration transducer. In such apparatus an inside end of a finned magnetostrictive transducer having a central tunnel is connected to the proximal end of a connecting portion located within said tunnel, which connecting portion transforms the ultrasonic vibration, and the distal end of said connecting portion is attached to the proximal end of a surgical tool. The configuration and mass of the surgical tool is such that amplification is obtained which makes the tool suitable, for example, for the fragmentation of tissue. A typical surgical handpiece in which the transducer, connecting portion and tool are attached serially end-to-end is disclosed in U.S. Pat. No. 4,223,676. A handpiece made in accordance with the present invention incorporating a folded resonator, wherein the connecting portion is located within the transducer, is more compact than said prior art handpiece and is consequently easier to handle and manipulate.

DESCRIPTION OF THE DRAWINGS

The invention will be more particularly described with reference to a prior art handpiece and a preferred embodiment of the present invention as illustrated in the accompanying drawings, in which:

Referring to FIG. 1 of the drawings, a typical prior art ultrasonic resonant vibrator comprises a transducer 1' connected, in line, to a connecting portion 2' and a surgical tool 3'. The length of each of the members of the device is determined by the individual sound velocities and operating frequency in the materials used for the resonant vibrator as hereinafter described and the overall length of the resulting handpiece is the sum of the lengths of its individual members and this results in a device which sometimes may be awkward and unwieldy for a surgeon to handle.

Said overall length is appreciably reduced by the provision of a folded resonator according to the present invention. The folded resonator is made possible by forming the magnetostrictive transducer from a plurality of elongated strips in a radially disposed finned configuration and providing a central tunnel extending along the central axis of the transducer, as illustrated in FIGS. 2 and 3 of the drawings.

Figure 1:
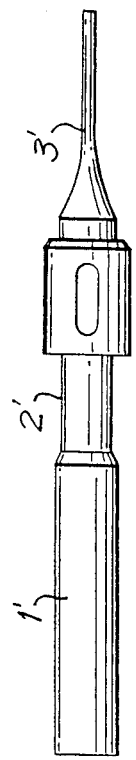
FIG. 1 is a schematic side elevation of an ultrasonic resonant vibrator showing the positioning of a transducer, connecting portion and tool as disclosed in the prior art.
Figure 2:
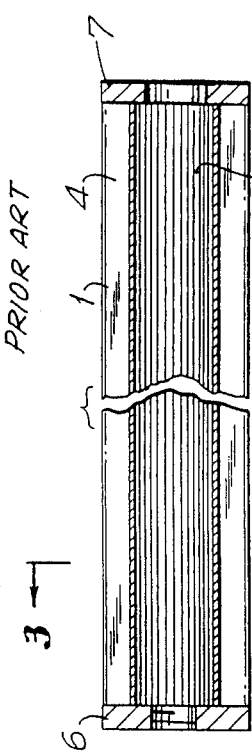
FIG. 2 is a side cross section of a finned transducer used in a vibrator according to the present invention.
Figure 3:
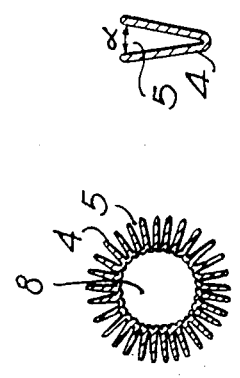
FIG. 3 is a cross section through line 3—3 of FIG. 2.

The magnetostrictive transducer illustrated in FIGS. 2 and 3 comprises a column 1 formed from a plurality, for example sixteen to forty-five preferably thirty-six of elongated strips of magnetostrictive material, each having a substantially V-shaped cross section. The magnetostrictive material is preferably a nickel alloy with an oxide coating.

Figure 4:
FIG. 4 is an enlarged cross section of a V-shaped elongated strip used in the transducer of FIG. 2.

Each of the arms 4 of each V is in touching contact with an arm of the V-shaped adjacent strip. Typically the space 5 between said arms is defined by an angle α (FIG. 4) which preferably is from 8° to 23°. The length of each of the elongated strips is determined by the operating frequency and sound velocity of the material used. The length of the vibrator is equivalent to the combination of connecting portion and tool. The dimensions of a preferred embodiment are given hereinafter.

The thickness of each strip is about 0.007 to 0.010 inch (about 0.018 to 0.025 cm.).

Each of the elongated strips is attached to each adjacent strip at its proximal end 6 and distal end 7. The attachment is preferably made by brazing or welding. In a preferred embodiment the attachment 6 is a face ring, made of suitable metal, for example stainless steel, brazed or welded to the finned column and having an internal screw thread (not shown) of about 0.375 inch (about 0.953 cm.) internal diameter. The attachment 7 also may be a face ring similar to 6. These face rings provide the resulting column with the desired rigidity and stiffness, and additionally one of them provides means for attachment of the connecting portion 2.

The column with radially extending fins has a longitudinal hole which defines a central tunnel 8, preferably of substantially circular cross section, centered along its central axis. In a preferred embodiment the column forming the transducer comprises thirty-six elongated strips of V-shaped cross section each having a length of about 2.6 inches (about 6.7 cm.). The diameter of the tunnel 8 is sufficient to accommodate an appropriate connecting portion and a preferred embodiment including such a member is illustrated in FIG. 5.

Figure 5:
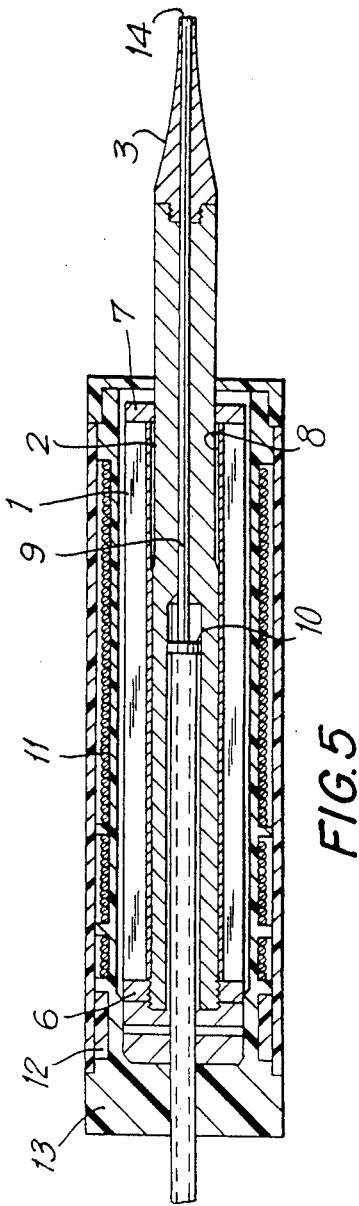
FIG. 5 is a partial side cross section and partial side elevation of part of a surgical handpiece incorporating an ultrasonic resonant vibrator of the invention.

FIG. 5 illustrates schematically an ultrasonic resonant vibrator comprising a finned magnetostrictive transducer 1 in which each of the elongated strips forming the fins is brazed or welded to a face ring 6 at its proximal end and to a face ring 7 at its distal end. The transducer has a central tunnel 8 within which is located a connecting portion 2, having a threaded proximal end. The connecting portion is attached to the transducer by screwing said threaded proximal end into the internal screw thread of face ring 6. In a preferred embodiment, said connecting portion comprises a stainless steel tube having a length of about 6.0 inches (about 15 cm) which is three quarters of a wave length, and an outside diameter of about 0.375 inch (about 0.953 cm.). In this embodiment the connecting portion has a central hole which contains an aspirator tube 9 held in place and having one or more sealing rings 10 at or near the nodal region of the connecting portion.

The field for driving the transducer is derived from an energizing coil 11.

The transducer and connecting portion are located in a plastic bobbin 12 within a plastic housing 13.

The embodiment illustrated in FIG. 5 is completed by a suitable tool 3 (not drawn to scale) attached to the distal end of the connecting portion in a conventional manner, e.g. through a threaded connector. The distal end of said tool has a tip 14 for the fragmentation of tissue. In this embodiment the combination of connecting portion 2 and surgical tool 3 may form a resonant member.

A shorter surgical handpiece of the type described containing a folded resonator according to the invention is less unwieldy and more convenient to use than the long handpieces of the prior art. Furthermore, it was found that a handpiece containing a finned transducer according to the invention required less input power than one incorporating a conventional prior art laminated transducer stack, indicating a further advantage of the folded resonator of the invention. In addition, the invention allows central, through, aspiration of unwanted tissue, which allows connection of surgical tubing at the proximal end of the handpiece, allowing for a smaller, uncluttered finger grip area.

Still further, it has been found that a surgical handpiece incorporating a folded resonator according to the invention may be used not only with a straight connecting portion but also with a curved connecting portion or a curved tool or other intermediate members.

We claim:

1. An ultrasonic resonant vibrator comprising a resonant member having a proximal end and a distal end and an ultrasonic vibration magnetostrictive transducer for generating ultrasonic vibrations which are transmitted from said transducer to said resonant member, wherein said transducer comprises a plurality of elongated strips of magnetostrictive material, each strip having a proximal end, a distal end and a substantially V-shaped cross section, wherein each arm of the V-shaped cross section is formed by the longitudinal length of each of said strips, each arm of each of said strips being attached along the radial length of each arm to each arm of each adjacent one said strips only at both the proximal end and the distal end to form an integral substantially rigid column having a central axis with fins extending radially relative to said axis, wherein said column defines a central tunnel with a proximal end and a distal end centered along said central axis, wherein at least part of said resonant member is located within said tunnel and is attached at its said proximal end to the proximal end of said tunnel.

2. A vibrator according to claim 1, in which said central tunnel is of substantially circular cross section.

3. A vibrator according claim 1, in which the attachment of the ends of each of said strips to the ends of each of said adjacent strips is made by brazing or welding.

4. A vibrator according to claim 1, in which each said arm of each of said strips is in touching contact with an arm of an immediately said adjacent one of said strips along the complete longitudinal length of the strip to form a radially extending fin which fin is one of a plurality of fins resulting from said plurality of elongated strips which form a radial pattern around said central tunnel extending the length of the resulting substantially rigid column.

5. A vibrator according to claim 1, in which said operating member is a surgical tool.

6. A vibrator according to claim 1, in which said connecting portion includes a central hole extending along its length and a tube for transporting fluid accommodated through said central hole.

* * * * *